United States Patent
Stegmann et al.

[11] Patent Number: 5,931,163
[45] Date of Patent: Aug. 3, 1999

[54] VALVE FOR SETTING THE FLOW OF A FLOW MEDIUM

[75] Inventors: Holger Stegmann, Lübeck; Eckhard Riggert, Ratekau, both of Germany

[73] Assignee: Drägerwerk AG, Lübeck, Germany

[21] Appl. No.: 08/874,372

[22] Filed: Jun. 19, 1997

[30] Foreign Application Priority Data

Oct. 23, 1996 [DE] Germany .............. 196 43 750

[51] Int. Cl.$^6$ .............. A61M 16/00; A62B 7/04; F16K 31/26; G05D 7/00
[52] U.S. Cl. .............. 128/204.26; 128/204.18; 128/204.21; 128/204.23; 128/205.24; 137/102
[58] Field of Search .............. 128/201.28, 204.23, 128/205.24, 207.12, 207.16, 204.18, 204.21, 204.24, 204.26, 204.27; 137/102

[56] References Cited

U.S. PATENT DOCUMENTS

| | | | |
|---|---|---|---|
| 3,063,461 | 11/1962 | Rudolph | 137/102 |
| 3,419,031 | 12/1968 | Hesse et al. | 137/102 |
| 3,561,466 | 2/1971 | Carden | 137/102 |
| 3,850,197 | 11/1974 | Ernst | 137/561 |
| 3,902,516 | 9/1975 | Rudolph | 137/102 |
| 4,334,532 | 6/1982 | Jackson | 128/204.26 |
| 4,354,520 | 10/1982 | Easley, Jr. | 137/543.23 |
| 4,733,919 | 3/1988 | Jacobs et al. | 303/28 |
| 4,770,165 | 9/1988 | Hayek | 128/205.26 |
| 4,815,452 | 3/1989 | Hayek | 128/205.26 |
| 4,930,498 | 6/1990 | Hayek | 128/204.21 |
| 5,007,420 | 4/1991 | Bird | 128/200.14 |
| 5,116,088 | 5/1992 | Bird | 235/319 |
| 5,323,773 | 6/1994 | Kobayashi | 128/205.24 |
| 5,425,358 | 6/1995 | McGrail et al. | 128/205.24 |
| 5,555,880 | 9/1996 | Winter et al. | 128/204.21 |
| 5,575,283 | 11/1996 | Sjoestrand | 128/204.23 |
| 5,664,562 | 9/1997 | Bourdon | 128/204.23 |
| 5,746,199 | 5/1998 | Bayron et al. | 128/205.24 |
| 5,762,102 | 6/1998 | Rimboym | 137/492.5 |
| 5,862,802 | 1/1999 | Bird | 128/204.18 |

FOREIGN PATENT DOCUMENTS

| | | | |
|---|---|---|---|
| 41 17 445 A1 | 12/1992 | Germany . | |
| 81987 | 6/1953 | Sweden | 128/205.24 |

*Primary Examiner*—John G. Weiss
*Assistant Examiner*—Joseph F. Weiss, Jr.
*Attorney, Agent, or Firm*—McGlew and Tuttle, P.C.

[57] ABSTRACT

A device with a valve for setting the flow of a flow medium, which has a passage channel with an inlet opening and with an outlet opening for the flow medium, and with a tongue-like valve element, which is arranged in the passage channel. The valve element is adjustable in a rotatably movable manner with an actuating device between two end positions. The device is adapted to users who need the flow medium at different pressure levels by providing a discharge opening branching off from the passage channel. The discharge opening is provided with a diaphragm opening having a predetermined gap geometry. The discharge opening with diaphragm opening is arranged in the range of pivoting of the valve element such that the discharge opening is closed in one of the end positions and the passage channel is switched essentially in the direction of flow at the same time.

12 Claims, 2 Drawing Sheets

VALVE FOR SETTING THE FLOW OF A FLOW MEDIUM

FIELD OF THE INVENTION

The present invention pertains to a valve for setting the flow of a flow medium, which valve has a passage channel with an inlet opening and with an outlet opening for the flow medium and is adjustable rotatably movably by means of an actuating device between two end positions with a valve element, which is arranged in the passage channel, as a result of which the flow is influenced as a function of the angle of rotation of the valve element.

BACKGROUND OF THE INVENTION

A valve of this type has become known from DE 41 17 445. The prior-art valve comprises a valve housing with a passage channel for the flow medium, in which a cylindrical body with a diaphragm opening, through which the flow medium flows, is inserted in a rotatingly movable manner. The flow cross section of the diaphragm opening is selected, depending on the angular position of the cylindrical body, such that there is a linear relationship between the rotary movement of the cylindrical body and the flow of the flow medium. The prior-art valve is designed for releasing the flow medium to a stationarily operating user.

In certain applications, e.g., in respiration technique, there occur variations in pressure during the operation on the discharge side of the valve, which are caused by inhalation phases and exhalation phases. Thus, a practically unthrottled gas flow is needed during the peaks of the inhalation phases to generate the inhalation pressure needed for respiration, while the pressure shall be reduced as quickly as possible at the time of the transition to the exhalation phase, while the breathing gas being fed in is throttled at the same time.

SUMMARY AND OBJECTS OF THE INVENTION

The primary object of the present invention is to adapt a valve of the above-described type to such users, who need the flow medium at different, oscillating pressure levels.

The object is accomplished by a discharge opening branching off from the passage channel with a diaphragm opening having a predetermined gap geometry being provided, which is arranged in the range of pivoting of the valve element such that the discharge opening is essentially closed in one of the end positions and the passage channel is thus essentially switched in the flow direction.

The advantage of the present invention is essentially to generate the pressure levels by throttling the flow medium in the passage channel while simultaneously relieving the pressure of the passage channel on the discharge side of the throttling point via a discharge opening, as a result of which an especially rapid and reproducible pressure variation is possible. The oscillation of the pressure is generated by means of a valve element arranged rotatingly movably in the valve housing of the valve, which can be pivoted between two stops, i.e., end positions. The passage channel is switched in the flow direction without throttling action by the valve element in one of the end positions of the valve element, and the discharge opening with the diaphragm opening is closed, so that a higher pressure value can build up in this position of the valve element, while the passage channel is closed by the valve element in the opposite end position, and the flow medium located on the discharge side of the valve element can escape into the discharge opening via the diaphragm opening. The pressure of the flow medium can be released almost completely in this position of the valve element. These limiting positions of the valve element are rarely needed during operation, but intermediate positions are set, in which a gas flow is still present in the passage channel and a certain amount of gas can escape at the same time via the discharge opening. Depending on the position of the valve element, the passage channel is throttled once more extensively and the diaphragm opening in the discharge opening is opened wider in return, so that the flow medium can escape via the discharge opening here. In the other case, when the valve element has been extensively pivoted out of the passage channel, the flow medium can flow through the passage channel nearly unhindered, and the diaphragm opening is covered by the valve element.

The valve according to the present invention can be used especially advantageously in respirators, in which different pressure levels must be set during the inhalation phase and the exhalation phase. It is important in respirators for the inhalation pressure to be available in full amount in the shortest time possible and for a rapid pressure relief to be possible, on the other hand, during the exhalation phase.

If, in addition, the diaphragm opening in the discharge opening is designed in the shape of a butterfly such that the largest flow cross sections are located in the area of the outer walls of the discharge opening and the smallest cross section is located in the area of the middle of the discharge opening, a pressure changing in proportion to the angle of rotation of the valve element is advantageously obtained on the discharge side of the discharge opening in a breathing gas line leading to a patient. Presetting of the pressure even simply via the angle of rotation of the valve element can be performed due to the proportionality between the angle of rotation and the pressure.

The valve element has an adjustment angle of about 90°.

One exemplary embodiment of the present invention is shown in the drawing and will be explained in greater detail below.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
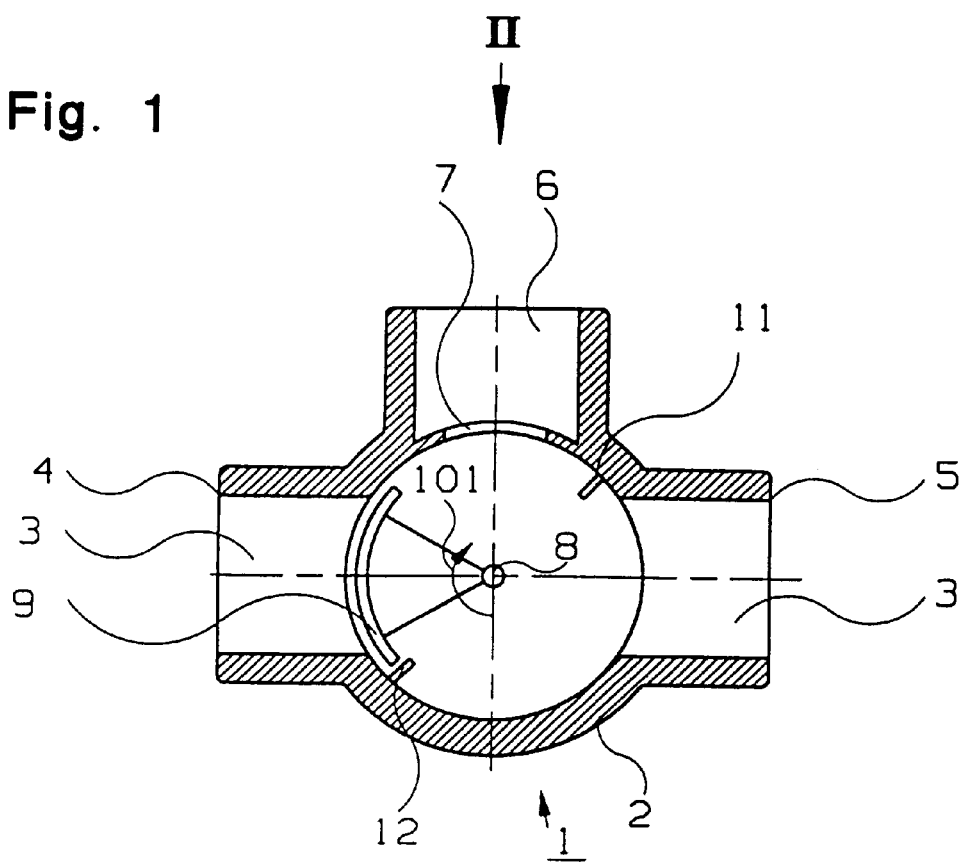
FIG. 1 is a longitudinal sectional view of a valve according to the present invention.
Figure 2:
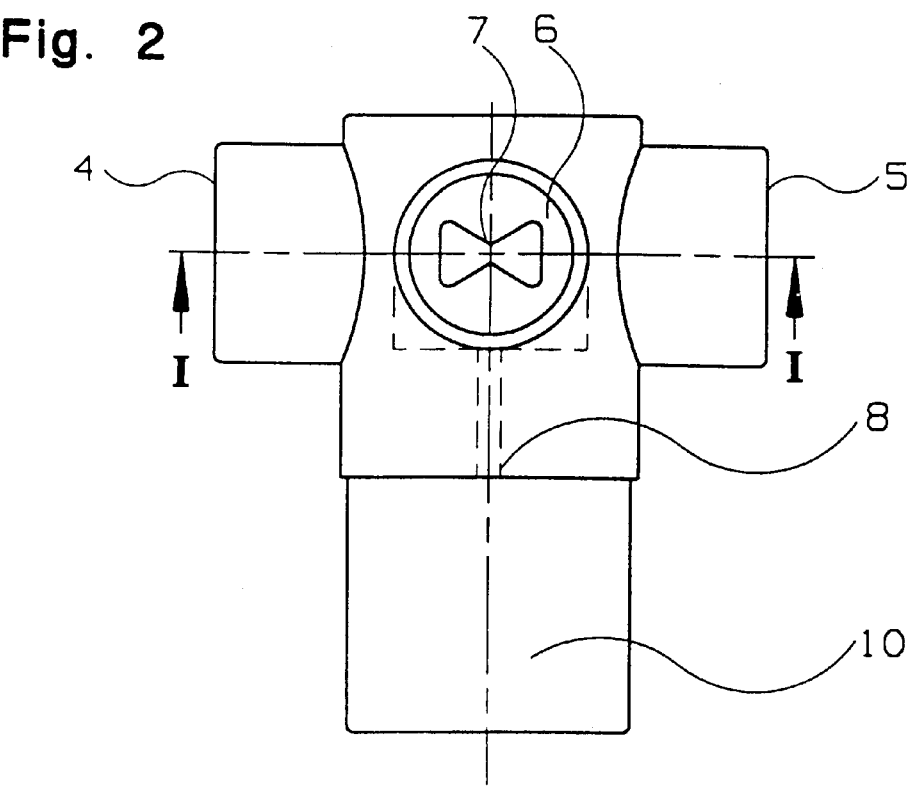
FIG. 2 is view I of the valve according to FIG. 1.

Referring to the drawings in particular, FIG. 1 shows a longitudinal section of a valve 1 along a section line I–I in FIG. 2. A passage channel 3 with an inlet opening 4 and an outlet opening 5 and a discharge opening 6 with a diaphragm 7, are located in a valve housing 2. The discharge opening 6 branches off perpendicularly from the passage channel 3. A tongue-like valve element 9, which is arranged within the valve housing 2 and is pivotable around a drive axis 8, is pivotable by means of an actuating device 10, FIG. 2, along the arrow 101 between the stops 11, 12. The valve element 9 is designed such that depending on the positioning within the valve housing 2, it covers the entire cross-sectional area of the inlet opening 4 or the area of the diaphragm 7. In the position of the valve element 9 shown in FIG. 1, the inlet opening 4 is closed and the diaphragm 7 is completely opened. If the valve element 9 is now adjusted in the direction of the stop 11 by means of the motor drive 10, the inlet opening 4 opens and the diaphragm 7 is closed to the same extent. With the inlet opening 4 fully opened, the flow medium can flow practically unhindered from the inlet opening 4 to the outlet opening 5 through the passage channel 3. Depending on the angular position of the valve element 9 between the stops 11, 12, a variable flow of the flow medium can escape into the discharge opening 6 via the diaphragm 7.

FIG. 2 shows view I of the valve 1 according to FIG. 1. Identical components are designated with the same reference numbers as in FIG. 1. The diaphragm 7 within the discharge opening 6 has the shape of a butterfly, with the largest flow cross sections at the walls of the discharge opening 6, while the smallest cross section is located in the middle of the discharge opening 6.

Figure 3:
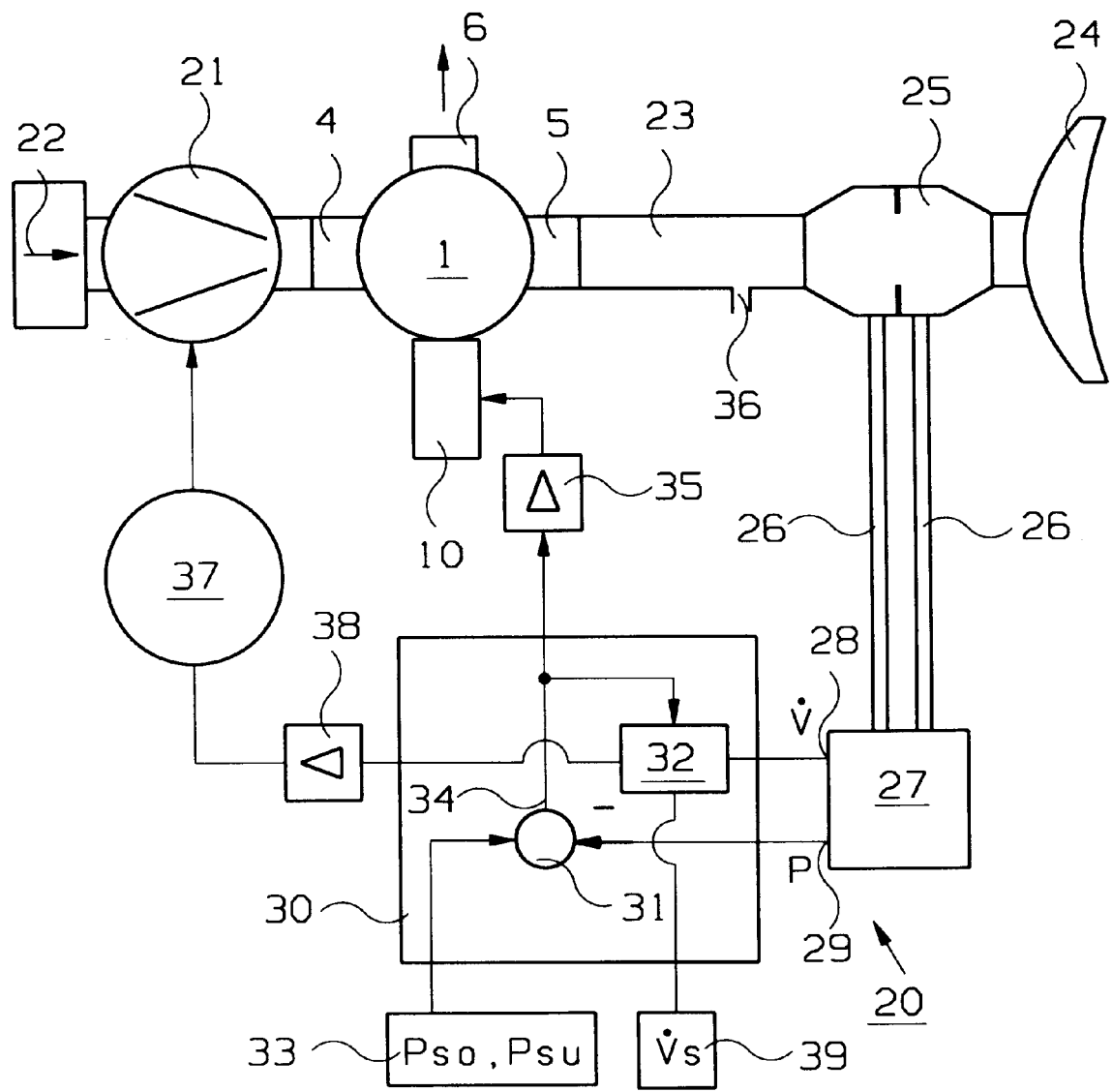
FIG. 3 is a schematic view of a respiration system with the valve according to FIG. 1.

FIG. 3 illustrates the use of the valve 1 according to the present invention in a respirator 20. Identical components are designated with the same reference numbers as in FIGS. 1 and 2. Air is drawn in by an inhalation supply means including a filter 22 and a fan 21 and is delivered via the valve 1 into a breathing gas line 23, at the end of which a breathing mask 24 for a patient, not shown in the Figure, is located. A measuring orifice 25, which is connected to a pressure-measuring device 27 via pressure-measuring lines 26 which detect the pressure drop over the measuring diaphragm 25, is located between the breathing mask 24 and the breathing gas line 23. The pressure-measuring device 27 has a first measuring output 28, via which a measured value proportional to the gas flow V in the breathing gas line 23 is sent, and a second measuring output 29, which sends a signal proportional to the pressure p in the breathing gas line 23. Both measuring outputs 28, 29 are connected to a control unit 30, in which all the calculation operations and controls necessary for the respiration are performed.

The control unit 30 contains as subunits a subtraction element 31 and a logic generator 32. The subtraction element 31 is connected to the second measuring output 29 and to a pressure set value setter 33, wherein the pressure set value setter 33 sends, alternating in time, an upper pressure limit $p_{so}$ for an inhalation phase and a lower pressure limit $p_{su}$ for an exhalation phase. By forming the difference between $p_{so}$ and $p_{su}$, on the one hand, and the pressure p measured by the pressure-measuring device 27, on the other hand, a difference signal, whose signal level is converted into a correcting variable for the electric motor drive 10 by means of an amplifier 35, is obtained at an output 34 of the subtraction element 31. If the upper pressure limit $p_{so}$, i.e., the inhalation phase, is present, the discharge opening 6 is extensively closed, depending on the inhalation demand, and the air being delivered by the fan 21 reaches the breathing mask 24 practically unhindered via the openings 4, 5 of the valve 1. If the lower pressure limit $p_{su}$, i.e., the exhalation phase, is present, the discharge opening 6 is opened and the gas present in the breathing gas line 23 or the gas exhaled by the patient via the breathing mask 24 can escape into the environment via the diaphragm 7, FIG. 2. A vent opening 36, via which gas can additionally flow into the environment to purge $CO_2$ from the breathing gas line 23, is also arranged in the course of the breathing gas line 23.

The fan 21 drawing in the air is driven by a motor 37, which receives its control signal from the logic generator 32 via an amplifier 38. The logic generator 32 is connected to a delivery volume set point setter 39 for the delivery volume $V_s$, to a first measuring output 28, as well as to the output 34 of the subtraction element 31. Via the first measuring output 28, the logic generator 32 receives information on the actual value of the gas flow V, and it compares it with the delivery volume set point $V_s$. At the same time, via the measured signal present at the output 34, the logic generator 32 receives information on the extent to which gas escapes via the discharge opening 6 during the period during which the upper pressure limit is set. If gas escapes via the discharge opening during the period during which the upper pressure limit is set, the speed of the motor 37 is reduced.

During normal respiration, the motor 37 is running at an essentially constant speed, and the pressure limits $p_{so}$ and $p_{su}$ needed for the respiration are set with the valve 1 by moving the valve element 9 between the stops 12, 11. A proportional change in the pressure p within the breathing gas line 23 is achieved during an adjustment of the angle of rotation of the valve element 9 due to the butterfly geometry of the diaphragm 7.

While a specific embodiment of the invention has been shown and described in detail to illustrate the application of the principles of the invention, it will be understood that the invention may be embodied otherwise without departing from such principles.

What is claimed is:

1. A device for setting the flow of a flow medium, comprising:

a passage channel with an inlet opening and with an outlet opening for the flow medium;

a valve element arranged in said passage channel;

an actuating device, said valve element being adjustable rotatably movable by means of said actuating device between two end positions for influencing flow as a function of an angle of rotation of said valve element;

a discharge opening branching off from said passage channel; and a diaphragm opening having a predetermined gap geometry provided in said discharge opening, said discharge opening being arranged in the range of pivoting of said valve element such that said discharge opening is essentially closed in one of said end positions and a direction of flow of said flow medium within said passage channel is essentially switched to flow through the passage channel unhindered;

control means for moving said valve element to control a pressure of the flow medium.

2. The device in accordance with claim 1, wherein said diaphragm opening has a butterfly-shaped design.

3. The device in accordance with claim 1, further comprising: one of a pressure and flow-measuring device for sending a measured signal proportional to one of a pressure and the flow at said passage channel downstream of said outlet opening, and a subtraction element for forming a correcting variable for said actuating device, said correcting variable being formed from said measured signal and a set point for the pressure ($p_s$) or flow ($V_s$).

4. The device in accordance with claim 2, further comprising: one of a pressure and flow-measuring device for sending a measured signal proportional to the pressure and flow at said passage channel downstream of said outlet opening, and a subtraction element for forming a correcting variable for said actuating device, said correcting variable being formed from said measured signal and a set point for the pressure ($p_s$) or flow ($V_s$).

5. The device in accordance with claim 1, further comprising: patient connection means including a breathing gas line connected to said passage channel outlet opening, said subtraction element and said set point being part of a control unit for setting the breathing gas flow or breathing gas pressure in said breathing gas line leading to a patient.

6. The device in accordance with claim 2, further comprising: patient connection means including a breathing gas line connected to said passage channel outlet opening, said subtraction element and said set point being part of a control unit for setting the breathing gas flow or breathing gas pressure in said breathing gas line leading to a patient.

7. The device in accordance with claim 3, further comprising: patient connection means including a breathing gas line connected to said passage channel outlet opening, said subtraction element and said set point being part of a control unit for setting the breathing gas flow or breathing gas pressure in said breathing gas line leading to a patient.

8. A process for setting the flow of a flow medium including setting a breathing gas flow or breathing gas pressure in a breathing gas line leading to a patient, the process comprising the steps of:

providing a passage channel with an inlet opening and with an outlet opening for the flow medium;

providing a valve element arranged in said passage channel;

adjusting rotatably said valve element between two end positions for influencing flow as a function of an angle of rotation of said valve element;

providing a discharge opening branching off from said passage channel;

providing a diaphragm opening having a predetermined gap geometry in said discharge opening, said discharge opening being arranged in the range of pivoting of the said valve element such that said discharge opening is essentially closed in one of said end positions; and controlling a pressure and direction of flow of said flow medium within said passage channel by said step of adjusting rotatably said valve element.

9. The process in accordance with claim 8, wherein said diaphragm opening is provided with a butterfly-shaped design.

10. The process in accordance with claim 8, further comprising:

sending a measured signal proportional to one of the pressure and the flow at said passage channel downstream of said outlet opening using one of a pressure and flow-measuring device; and forming a correcting variable for said actuating device using a subtraction element, said correcting variable being formed from said measured signal and a set point for the pressure ($P_s$) or flow ($V_s$).

11. The process in accordance with claim 8, further comprising:

connecting a patient to said passage channel outlet opening via a breathing gas line, said subtraction element and said set point being part of a control unit setting the breathing gas flow or breathing gas pressure in said breathing gas line leading to the patient.

12. A process for controlling a flow medium in a breathing gas line of a patient, the process comprising the steps of:

providing a passage channel with an inlet opening and with an outlet opening for the flow medium, said outlet opening being in communication with an end of the breathing gas line;

providing a discharge opening branching off from said passage channel;

providing an inhalation supply means for supplying the flow medium to said inlet opening;

providing a valve element movably arranged in said passage channel between a first position and a second position, said valve element in said first position closing said inlet opening, said valve element in said second position closing said discharge opening, said valve element partially closing said inlet opening and said discharge openings when said valve element is positioned between said first and second positions;

measuring pressure and flow of the flow medium in the breathing gas line;

providing predetermined pressure limits for inhalation and exhalation of the patient;

comparing said predetermined pressure limits with measured pressure in the breathing line;

moving said valve element between said first and second positions to control a pressure and flow of the flow medium in the breathing gas line during inhalation and exhalation based on said measured pressure and flow, and on said predetermined pressure limits.

* * * * *